United States Patent
Gregory et al.

(10) Patent No.: US 9,891,193 B2
(45) Date of Patent: Feb. 13, 2018

(54) REAGENT IMPREGNATED SWIPE FOR CHEMICAL DETECTION

(71) Applicant: Massachusetts Institute of Technology, Cambridge, MA (US)

(72) Inventors: Kerin E. Gregory, Bolton, MA (US); Roderick R. Kunz, Acton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/832,905

(22) Filed: Mar. 15, 2013

(65) Prior Publication Data

US 2014/0030816 A1  Jan. 30, 2014

Related U.S. Application Data

(60) Provisional application No. 61/674,980, filed on Jul. 24, 2012.

(51) Int. Cl.
*G01N 27/00* (2006.01)
*G01N 27/62* (2006.01)
*G01N 1/02* (2006.01)

(52) U.S. Cl.
CPC .............. *G01N 27/622* (2013.01); *G01N 1/02* (2013.01); *G01N 2001/028* (2013.01)

(58) Field of Classification Search
CPC .................................................... G01N 27/622
(Continued)

(56) References Cited

U.S. PATENT DOCUMENTS 4,752,448 A   6/1988  Wells et al.
5,988,002 A   11/1999 Danylewych-May et al.
(Continued)

FOREIGN PATENT DOCUMENTS

| EP | 1145005 | 10/2001 |
|---|---|---|
| EP | 1844189 | 10/2007 |
| WO | 1999005319 A2 | 2/1999 |
| WO | 2007066240 | 6/2007 |
| WO | 2011144743 A1 | 11/2011 |

OTHER PUBLICATIONS

3-Pyridinecarboxamide (nicotinamide) (UNEP Publications Oct. 2002) accessed by examiner at [http://www.inchem.org/documents/sids/sids/98920.pdf].*
"18-crown-6" accessed by examiner at [http://www.chemical-land21.com/lifescience/phar/18-CROWN-6.htm] on Apr. 1, 2014.*
(Continued)

*Primary Examiner* — Christine T Mui
*Assistant Examiner* — Emily R. Berkeley
(74) *Attorney, Agent, or Firm* — Thomas J. Engellenner; Reza Mollaaghababa; Pepper Hamilton LLP

(57) ABSTRACT

The invention is directed to a swipe with at least one ionization reagent associated with the swipe for detecting target analytes and methods of detecting the target analyte molecules that can indicate the presence of, for example, explosives, narcotics, chemical warfare agents, biological warfare agents, or toxins. The swipe can be used to transfer molecules from a surface to the swipe for further analysis. In particular, the swipes can include an ionization reagent that is preferably a low volatility compound and capable of forming ionization reagent-analyte complexes with target analytes. The swipe can also include multiple ionization reagents with different volatilities such that they are released sequentially during a thermal ramp-up. Alternatively, the swipe can have multiple ionization reagents associated with spatially separated portions of the swipe such that they can be releasable sequentially to detect multiple target analytes.

23 Claims, 2 Drawing Sheets

(58) Field of Classification Search
USPC .......................................................... 422/68.1
See application file for complete search history.

(56) References Cited

U.S. PATENT DOCUMENTS

| | | | |
|---|---|---|---|
| 6,287,780 | B1 | 9/2001 | Schmidt et al. |
| 6,627,444 | B1* | 9/2003 | Goledzinowski et al. ........ 436/8 |
| 7,439,496 | B2* | 10/2008 | Stott et al. ..................... 250/282 |
| 8,119,984 | B2 | 2/2012 | Shabanowitz et al. |
| 8,304,251 | B2 | 11/2012 | Haas et al. |
| 2004/0157344 | A1 | 8/2004 | Wang et al. |
| 2005/0288616 | A1* | 12/2005 | Bozenbury et al. .............. 604/1 |
| 2008/0101995 | A1 | 5/2008 | Gabowitcz et al. |
| 2008/0128608 | A1* | 6/2008 | Northen et al. .............. 250/282 |
| 2008/0245963 | A1 | 10/2008 | Land et al. |
| 2009/0032701 | A1 | 2/2009 | Rodier et al. |
| 2009/0039243 | A1 | 2/2009 | Wynn et al. |
| 2009/0078862 | A1 | 3/2009 | Rodier et al. |
| 2009/0269855 | A1 | 10/2009 | Wang et al. |
| 2010/0047849 | A1 | 2/2010 | Caulfield et al. |
| 2010/0291704 | A1 | 11/2010 | Cody |
| 2011/0081723 | A1* | 4/2011 | Miller et al. .................... 436/56 |
| 2011/0101216 | A1 | 5/2011 | Musselman |
| 2012/0119079 | A1 | 5/2012 | Ouyang et al. |
| 2012/0149006 | A1 | 6/2012 | Padilla De Jesus et al. |
| 2012/0181421 | A1* | 7/2012 | Satoh ................... H01J 49/142 250/282 |

OTHER PUBLICATIONS

Oscar Yanes, Hin-Koon Woo, Trent R. Northen, Stacey R. Oppenheimer, Leah Shriver, Jon Apon, Mayra N. Estrada, Michael J. Potchoiba, Rick Steenwyk, Marianne Manchester, and Gary Siuzdak "Nanostructure Initiator Mass Spectrometry: Tissue Imaging and Direct Biofluid Analysis" Anal. Chem. 2009, 81, 2969-2975.*

Hadis Morkoç "Handbook of Nitride Semiconductors and Devices, Materials Properties, Physics and Growth" Jul. 30, 2009.*

Iarc Monographs vol. 73 "Hexachloroethane" was accessed by the examiner from "http://monographs.iarc.fr/ENG/Monographs/vol73/mono73-15.pdf" on Dec. 22, 2014.*

Brodbelt, J. S.; Liou, C. C., New frontiers in host-guest chemistry—the gas phase. Pure and Applied Chemistry 1993, 65 (3), 409-414.

Chu, I. H.; Zhang, H.; Dearden, D. V., Macrocyclic chemistry in the gas phase—intrinsic cation affinities and complexation rates for alkali-metal cation complexes of crown-ethers and glymes. Journal of the American Chemical Society 1993, 115 (13), 5736-5744.

de Perre, C.; Prado, A.; McCord, B. R., Rapid and specific detection of urea nitrate and ammonium nitrate by electrospray ionization time-of-flight mass spectrometry using infusion with crown ethers. Rapid Communications in Mass Spectrometry 2012, 26 (2), 154-162.

Dietrich, B.; Kintzinger, J. P.; Lehn, J. M.; Metz, B.; Zahidi, A., Stability, molecular-dynamics in solution, and x-ray structure of the ammonium cryptate NH4+ subset of 2.2.2.PF6. Journal of Physical Chemistry 1987, 91 (27), 6600-6606.

Eiceman, G. A.; Yuan-Feng, W.; Garcia-Gonzalez, L.; Harden, C. S.; Shoff, D. B., Enhanced selectivity in ion mobility spectrometry analysis of complex mixtures by alternate reagent gas chemistry. Analytica Chimica Acta 1995, 306 (1), 21-33.

Evans, C. S.; Sleeman, R.; Luke, J.; Keely, B. J., A rapid and efficient mass spectrometric method for the analysis of explosives. Rapid Communications in Mass Spectrometry 2002, 16 (19), 1883-1891.

Ewing, R. G.; Atkinson, D. A.; Eiceman, G. A.; Ewing, G. J., A critical review of ion mobility spectrometry for the detection of explosives and explosive related compounds. Talanta 2001, 54 (3), 515-529.

Flanigan, P. M.; Brady, J. J.; Judge, E. J.; Levis, R. J., Determination of Inorganic Improvised Explosive Device Signatures Using Laser Electrospray Mass Spectrometry Detection with Offline Classification. Analytical Chemistry 2011, 83 (18), 7115-7122.

Graf, E.; Kintzinger, J. P.; Lehn, J. M.; Lemoigne, J., Molecular recognition—selective ammonium cryptates of synthetic receptor molecules possessing a tetrahedral recognition site. Journal of the American Chemical Society 1982, 104 (6), 1672-1678.

Kozole, J.; Tomlinson-Phillips, J.; Stairs, J. R.; Harper, J. D.; Lukow, S. R.; Lareau, R. T.; Boudries, H.; Lai, H.; Brauer, C. S., Characterizing the gas phase ion chemistry of an ion trap mobility spectrometry based explosive trace detector using a tandem mass spectrometer. Talanta 2012, 99, 799-810.

Lawrence, A. H.; Neudorfl, P., Detection of ethylene glycol dinitrate vapors by ion mobility spectrometry using chloride reagent ions. Analytical Chemistry 1988, 60 (2), 104-109.

Maleknia, S.; Brodbelt, J., Cavity-size-dependent dissociation of crown-ether ammonium ion complexes in the gas-phase. Journal of the American Chemical Society 1993, 115 (7), 2837-2843.

More, M. B.; Ray, D.; Armentrout, P. B., Intrinsic affinities of alkali cations for 15-crown-5 and 18-crown-6: Bond dissociation energies of gas-phase M+-crown ether complexes. Journal of the American Chemical Society 1999, 121 (2), 417-423.

Park, K.-M.; Kim, H. J.; Moon, S.-H.; Vittal, J. J.; Jung, J. H.; Lee, S. S., Surprisingly stable ammonium ion complex of a non-cyclic crown-type polyether: Solid and solution studies. New Journal of Chemistry 2010, 34 (4), 603-606.

Sassine, A.; Martins-Junior, H. A.; Lebre, D. T.; Valli, F.; Pires, M. A. F.; Vega, O.; Felinto, M. C. F. C., An electrospray ionization tandem mass spectrometric study of p-tert-butylcalix[6]arene complexation with ammonium hydroxide, and ammonium and sodium ions. Rapid Communications in Mass Spectrometry 2008, 22 (3), 385-393.

Späth, A.; Koenig, B., Molecular recognition of organic ammonium ions in solution using synthetic receptors. Beilstein Journal of Organic Chemistry 2010, 6.

Taylor, V. F.; March, R. E.; Longerich, H. P.; Stadey, C. J., A mass spectrometric study of glucose, sucrose, and fructose using an inductively coupled plasma and electrospray ionization. International Journal of Mass Spectrometry 2005, 243 (1), 71-84.

Tsai, C.-W.; Midey, A.; Wu, C.; Yost, R. A. Analysis of ammonium nitrate/urea nitrate with crown ether and sugar as modifiers, American Society for Mass Spectrometry, Denver, 2011.

Badu-Tawiah, A. K.; Campbell, D. I.; Cooks, R. G., Reactions of microsolvated organic compounds at ambient surfaces: Droplet velocity, charge state, and solvent effects. Journal of the American Society for Mass Spectrometry 2012, 23 (6), 1077-1084.

Benassi, M.; Wu, C.; Nefliu, M.; Ifa, D. R.; Volny, M.; Cooks, R. G., Redox transformations in desorption electrospray ionization. International Hournal of Mass Spectrometry 2009, 280, 325-240.

Fieser, M., Fiesers' Reagents for Organic Synthesis, vol. 27, John Wiley & Sons, 2011. Table of contents.

McDougall, J.L.; Simkins, R.J.J., The identification of traces of explosives by field spot tests in Ministry of Defense Explosives Research and Development Establishment, Technical Report No. 122, Mar. 1973.

Smith, M., March's Advanced Organic Chemistry: Reactions, Mechanisms and Structure, 7th Edition, Wiley & Sons, 2013. Table of contents.

Sundberg, R. J.; Carey, F. A., Advanced Organic Chemistry, Part B: Reactions and Synthesis, 5th Edition, Springer, 2007. Table of contents.

Urbansky, E.T.; Magnuson, M.L.; Freeman, D.; Jelks, C., Quantitation of perchlorate ion by electrospray ionization mass spectrometry (ESI-MS) using stable association complexes with organic cations and bases to enhance selectivity, Journal of Analytical Atomic Spectrometry 1999, 14, 1861-1866.

PCT Notification of Transmittal of the International Search Report and the Written Opinion of the International Searching Authority, or the Declaration, PCT/US2013/051676, dated May 27, 2014 (11 pages.).

International Search Report and Written Opinion for PCT/US2013/051671, dated Apr. 4, 2014 (10 pages).

Office Action from related U.S. Appl. No. 13/948,423 dated Aug. 10, 2016.

(56) References Cited

OTHER PUBLICATIONS

Li, Yongtao et al. "Reversed-phase liquid chromatograph/electrospray ionization/mas spectrometry with isotope dilution for the analysis of nitrate and nitrite in water" Journal of Chromatograph A, A 1218, pp. 476-483 (@011).

* cited by examiner

REAGENT IMPREGNATED SWIPE FOR CHEMICAL DETECTION

REFERENCE TO RELATED APPLICATION

This application claims the priority of U.S. Provisional Patent Application No. 61/674,980 filed Jul. 24, 2012 entitled "Reagent Impregnated Swipe For Thermal Desorption Release And Chemical Detection With Ambient Ionization Technology."

GOVERNMENT RIGHTS

This invention was made with U.S. government support under Interagency Agreements HSHQDC-09-X-00439 and HSHQPM-12-X-0057 by the U.S. Department of Homeland Security, Science and Technology Directorate, and performed by MIT Lincoln Laboratory under Air Force Contract No. FA8721-05-C-0002. The U.S. government has certain rights in the invention.

FIELD OF THE INVENTION

The present invention concerns contraband detection and, in particular, sampling methods and materials for spectrometric detection of explosives, toxins, narcotics and the like.

BACKGROUND OF THE INVENTION

The evolving threats posed by concealed explosives or the intentional release of toxic chemicals demand new ways to detect these threats and protect the public. Typically, the techniques for identifying threat molecules involve ionizing a sample and then detecting whether the threat molecule (analyte) is present. The detection mechanisms include ion mobility spectrometry (IMS), differential mobility spectrometry (DMS), field asymmetric ion mobility spectrometry (FAIMS), and mass spectrometry (MS), all of which rely upon ionization of the analyte or a complex that includes the analyte. In fact, one of these techniques (IMS) is currently used in nearly every airport in the United States as a means to prevent concealed explosives from getting on aircraft.

Given the importance of these techniques to public safety, considerable effort has been devoted to develop the best means to collect the sample from the environment, present the sample to the instrument, and to also ionize it efficiently and if possible selectively, in order to provide the greatest detection capability.

In almost all instances, ionization is achieved selectively by performing the ionization under ambient-pressure conditions in the presence of an ionization reagent in a technique known as ambient-pressure ionization (API) (also sometimes called atmospheric-pressure chemical ionization). In API, the target analyte is drawn into a space containing both an ionization source and the ionization reagent, and ionization of the target molecule takes place through ion-molecule collisions. The ionization reagent is selected such that rapid achievement of charge equilibrium results in charge or proton transfer from the reagent to the target molecule.

Since many of the explosive and chemical threats have low vapor pressure and exist as traces of particulates or thin films on surfaces, the most common way to collect the sample requires a swipe or swab substrate which provides a physical mechanism to both collect and preconcentrate a sample taken from a surface of a suspect object for subsequent presentation to the ionization space of the detection instrument. The substrate media, which is called a "swipe," can be thermally heated to desorb the target analyte into the vapor phase for subsequent ionization and detection. This methodology is currently used in fielded IMS systems that detect explosives, where detection relies on efficient collection and presentation of low-vapor analytes such as 2,4,6-trinitrotoluene (TNT), 1,3,5-trinitro-1,3,5-triazacyclohexane (RDX) and pentaerythritol tetranitrate (PETN) into the instrument, and use of ionization reagents that enhance the formation of negative ions via chloride adduction, such as methylene chloride.

In such explosive detection systems, the substrate is typically positioned in a thermal desorber located on the inlet side of the detection system. Thermal heating of the solid particles on the swipe induces a solid-to-vapor phase transition and releases the analyte molecules as a vapor, usually guided into the sensor inlet by a carrier gas, and the ionization reagent is introduced as a vapor within a separate carrier gas. Properties of commercially-available swipe media have been optimized over the years for increased efficiency of particle collection from surfaces (mechanical or electrostatic), efficient transfer and release of analyte into the chemical sensor, thermal stability, and low chemical background of the substrate.

SUMMARY OF THE INVENTION

The invention is directed to a swipe with at least one ionization reagent associated with the swipe for detecting target analytes and methods of detecting the target analyte molecules that can indicate the presence of, for example, explosives, narcotics, chemical warfare agents, biological warfare agents, or toxins. The swipe can be used to transfer molecules from a surface to the swipe for further analysis. In particular, the swipes can include an ionization reagent that is preferably a low volatility compound and capable of forming ionization reagent-analyte complexes with target analytes. The swipe can also include multiple ionization reagents with different volatilities such that they are release sequentially during a thermal ramp-up. Alternatively, the swipe can have multiple ionization reagents associated with spatially separated portions of the swipe such that they can be releasable sequentially to detect multiple target analytes.

Products and methods are disclosed that employ an improved swipe that contains both a substrate optimized for collecting chemical traces and an ionization reagent to improve the ionization probability and/or increase the resultant mass of the target analyte.

In one aspect of the invention, swipes are disclosed for detection of an analyte molecule that include a substrate configured to collect a sample for analysis; and at least one ionization reagent associated with the substrate and capable of reacting with an analyte if present in the sample to improve detection. In some embodiments, the ionization reagent is capable of forming a reagent-analyte complex with an analyte if present in the sample, e.g., the ionization reagent can generate a charged complex with an analyte if present in the sample upon release from the substrate and ionization. The ionization reagent is releasable into a carrier gas along with any target analyte molecules captured by the substrate during desorption in a detection instrument.

In certain embodiments, the ionization reagent is a low volatility compound. For example, the ionization reagent can have a vapor pressure less than 1 or $10^{-1}$ or $10^{-2}$ or $10^{-3}$ Torr.

In certain embodiments, the ionization reagent is adapted to form a host-guest complex with the analyte. The ionization reagent can include at least one of β-keto esters, crown ethers, glymes, sugars, cryptands, amides, amines, chlorinated alkanes, organic bases, ionic dyes, and cavitands.

The swipes of the present invention can further include a plurality of ionization reagents. The plurality of ionization reagents can be associated with spatially separated portions of the swipe or the plurality of ionization reagents can be uniformly applied to substrate. The plurality of ionization reagents having different vaporization temperatures.

In other embodiments, the swipe can also include one or more internal standards.

The substrate component of the swipe can be formed from various materials, including least one of paper, fabric, cloth, fibrous matte, gauze, cellulose, cotton, flax, linen, synthetic fibers and blends of such materials. The substrate should be clean, and free of extractables, such dirt, grime, contaminants, incidental materials or fabrication residues. In certain preferred embodiments, the substrate has an extractables content of less than 3% or 2% or 1% or 0.1% or 0.01% during desorption. The substrate is preferably also capable of resisting decomposition at temperatures up to about 300° C.

In another aspect of the invention, methods of detecting a target analyte are disclosed, which can include the steps of swiping a surface with a swipe having a substrate configured to collect a sample for analysis and at least one ionization reagent associated with the substrate; ionizing molecules present on the swipe following contact with the surface; and analyzing the ionized molecules to detect the target analyte. The methods can further include forming at least one charged complex of the reagent and a target analyte; and analyzing at least one charged species of the reagent-analyte complex to detect the target analyte.

The step of analyzing the ionized material can further include detection of the charged analyte or charged complex by ion mobility spectrometry, differential mobility spectrometry, field asymmetric spectrometry or mass spectrometry. In one preferred embodiment, the ionized molecules are detected by ion mobility spectrometry. Alternatively, they can be detected by mass spectrometry.

The methods of the present invention can further include heating the swipe to vaporize the molecules present on the swipe and the step of ionizing the molecules can be conducted by ionizing the molecules under ambient pressure conditions. In certain embodiments, the ionization reagent is a low volatility compound. The methods can further include employing swipes that include multiple ionization reagents. For example, the swipe can include multiple ionization reagents associated with spatially separated portions of the swipe and the step of ionization can further include heating different portions of the swipe in sequence. Alternatively, two or more ionization reagents having different vapor pressures can be applied to the substrate and the step of ionizing can further include exposing the swipe to a thermal gradient such that the ionization reagents are released sequentially.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

DETAILED DESCRIPTION OF THE INVENTION

Figure 1:
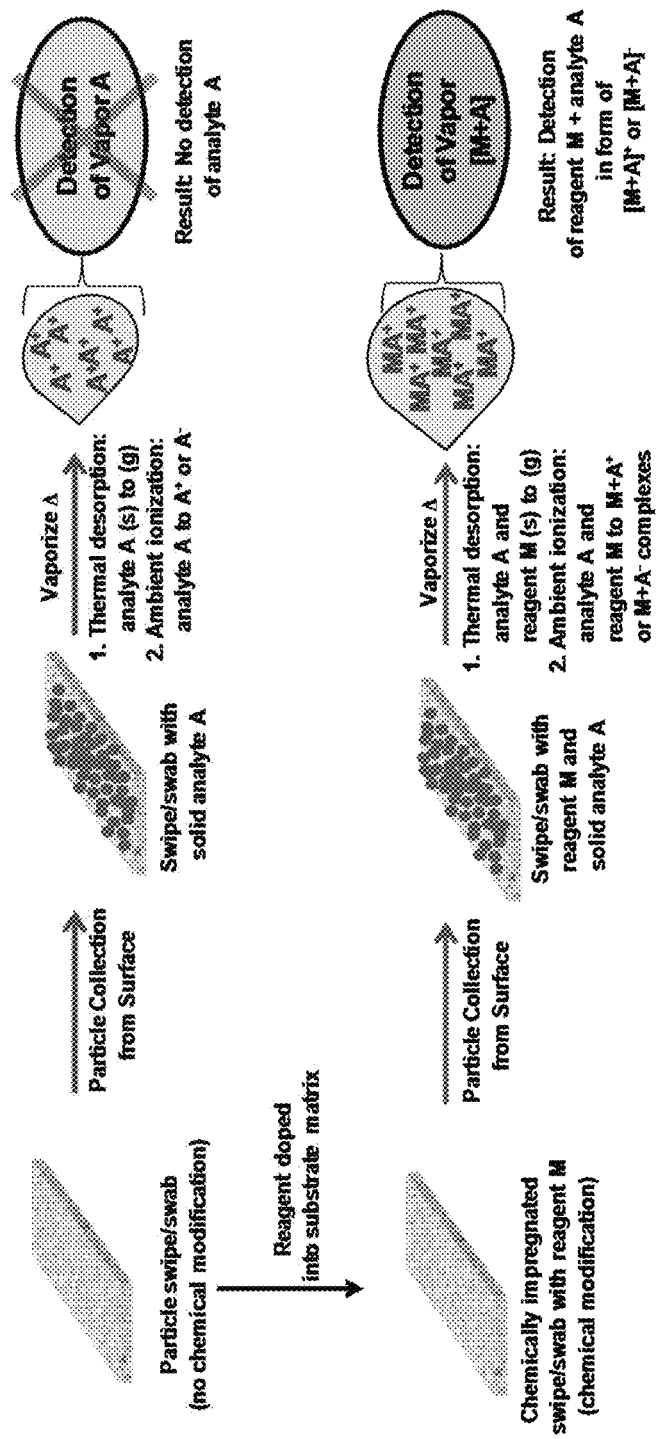
FIG. 1 illustrates the concept of doping a chemical reagent into substrate media (usually a fabric of polyester, muslin, or cotton) entraining low volatility compounds until released by desorption (e.g. thermal) and provides a flow diagram comparing a reagent impregnated swipe approach (bottom flow diagram) versus the use of swipes with no chemical modification (top flow diagram)

Detection of explosives is a subject of continuing strong interest in analytical chemistry, driven by threats to civil society and by environmental problems associated with explosives residues. Some requirements for an ideal method can include (i) high sensitivity, (ii) applicability to involatile and thermally unstable analytes, (iii) high specificity to minimize the chance of false positives or false negatives, (iv) rapid response times, and (v) no sample preparation or handling. No methods currently available meet all these criteria.

In one aspect of the invention a new kind of swipe is disclosed that embeds a solid-phase (or liquid-phase) ionization reagent directly into the swipe, providing several distinct advantages. The invention permits ionization reagents to be used that are not amenable to entrainment in a carrier gas in conventional spectrometric systems, thus making accessible a wider range of ionization reagents, including those of higher molecular weight. This advantage allows ionization reagents that are unreliably delivered as a vapor in a carrier gas by virtue of their high molecular weights (e.g., >400 Da) and solid states at room temperature to form higher molecular weight and/or higher vapor pressure adducts with the target analyte, making detection possible. The variability in ionization reagents and the location of the ionization reagents on the swipes further allows the operator to choose the ionization reagent(s) that best matches the suspected threat. The invention also permits rapid, automated analyses for multiple analytes where the swipe is heated and analyzed in zones, with each zone optimized for the API of specific target analytes. Internal standards can also be impregnated into the swipe to improve the quantification of the analysis method. In each of these embodiments, the objective is to broaden the range, type, and performance of ionization reagents which in turn allows for the API of a wider range of threat chemicals and at better sensitivity and precision.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments.

Such modifications and variations are intended to be included within the scope of the present invention.

All publications, patents and patent applications cited herein, whether supra or infra, are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art. In case any further explanation might be needed, some terms have been further elucidated below.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. For instance, a concentration value of about 30% can mean a concentration between 27% and 33%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

Mass spectrometry is an analytical process for identifying a compound or compounds in a sample by assessing the molecular weight, chemical composition and structural information based on the mass-to-charge ratio of charged particles. Mass spectrometry is widely considered to have the best specificity of any technique applicable to a broad class of explosive compounds. In general, a sample undergoes ionization to form charged particles as ions; these charged particles are then passed through electric and/or magnetic fields to separate them according to their mass-to-charge ratio.

The ionization process can be performed by a wide variety of techniques, depending on the phase (solid, liquid, gas) of the sample and the efficiency of the target analyte(s) in question. Some examples of ion sources can include electron ionization, glow discharge ionization, resonant ionization, field desorption, fast atom bombardment, thermospray, desorption/ionization on silicon, atmospheric pressure chemical ionization, spark ionization, inductively coupled plasma ionization, secondary ionization by sputtering ion beams off the target's surface, and thermal ionization.

Ambient-pressure ionization, collision-induced ionization, and atmospheric-pressure chemical ionization refer to a characterization technique in which picogram to microgram quantities of an analyte can be analyzed. The process generally refers to a chemical sample that is introduced into an ionization region as either a solid, liquid, or gas. In the ionization region, the analyte is in contact with other gases and ions that are part of the ionization region. Additional ions are produced through the collision of the analyte molecules with ions within the ionization reagent that are present in the ion source, electro-magnetic device. Inside the ion source, the ionization reagent is present in large excess compared to the analyte. Electrons and/or ions entering the source will preferentially ionize the ionization reagent. Collisions with other ionization reagent molecules will induce further ionization, creating positive and/or negative ions of the analyte. The ions are drawn into the spectrometer by either a carrier gas or focused into a beam by an electromagnet, then separated into individual beams based on the mass/charge ratio of the ions. The ion beams are separated in a mass spectrometer and collected either sequentially in a single detector or simultaneously in a set of multiple detectors to yield isotopic ratios. Highly accurate results require that sample cross-contamination be minimized.

The traditional methods for explosives detection usually involve wiping the ambient surface with a special material wipe followed by thermal desorption/gas phase ionization of the explosive compounds in the presence of an ionization reagent. However, this method is not ideal for the detection of thermally labile explosives or explosives which have low vapor pressures. Low-volatility explosives are those which release very small amounts of the explosive vapor, typically at parts per trillion levels or lower, even when heated, making it extremely difficult to detect.

The terms "desorption," "desorb" and "desorbing" as used herein refer to technology of increasing the volatility of molecules, for example target analytes, such that they can be removed (separated) from the solid. Thermal desorption is not incineration, but uses heat and a flow of inert gas to extract volatile and semi-volatile organics retained in a sample matrix or on a sorbent bed. The volatilized compounds are then either collected or thermally destroyed.

The ionization reagents are typically selected for rapid charge or proton transfer from the reagent to the target analyte. Ionization reagents can affect the number and size of peaks an analyte produces in a mass spectrometry signature and can suppress peaks entirely. An optimal ionization reagent is capable of forming readily identifiable analyte ions, while suppressing ion formation for molecules which are not of interest. Detection typically relies on efficient collection and presentation of low vapor analytes into the instrument, and use of high volatility, gaseous ionization reagents that enhance the formation of either positive or negative ions. However, detection of a broader range of target analytes is hindered by the dependence on high volatility gases as ionization reagents.

To overcome this limitation, swipe substrates with ionization reagents impregnated into them were developed. Through co-vaporization of both the target analyte and the ionization reagent into the ionization space of an instrument, the two become in communication with one another resulting in ionization of the target analyte. The ionization can result in the formation of a complex between the target analyte and the ionization reagent with unique characteristics for detection. The complex can have detectable properties that include shifts in mass or ion mobility for increased selectivity. Also, if the target analyte was previously undetectable, formation of a complex can allow detection. In some cases, the complex will be detectable with lower background and therefore increase sensitivity.

FIG. 1 illustrates the concept of doping a chemical reagent or ionization reagent into a substrate material or swipe (usually made of a fabric of polyester, muslin, or cotton). The substrate will entrain low volatility compounds until released by desorption (e.g. thermal). FIG. 1 also provides a flow diagram comparison of the proposed ionization reagent impregnated swipe approach versus the use of current swipes with no chemical modification. The example shown is for chemical sensors with sample introduction via thermal desorption and detection of the ionized reagent+target analyte adduct in either positive or negative ion mode.

Ionization Reagents

The chemicals used in conventional ambient ionization sources are introduced within the detection system as a vapor reagent in the carrier gas. This limits the list of reagents to high vapor pressure and/or lower molecular weight candidates. Low volatility compounds often provide higher affinity to the desired target analyte and increase probability of detection not achieved with higher volatility reagents. In addition, ionization reagents can be used that are not otherwise amenable to entrainment in a carrier gas, thus making accessible a wider range of ionization reagents, including those of high molecular weight. One advantage of high molecular weight (>400 Da) reagents is that they can possess more complex molecular structures and thus they can act as better ionization reagents. These high molecular weight reagents are solids at room temperature and cannot be easily or reliably delivered as a vapor in a carrier gas. However, by virtue of their high molecular weight, they can form high-molecular adducts or complexes with the target analyte making detection much easier.

The terms "low volatility" and "low vapor pressure" as used herein are intended to describe compositions that do not readily evaporate or sublimate at room temperature (e.g., at about 25° C.). Typically such low volatility compositions are solids or viscous liquids and have a vapor pressure at room temperature of less than 1 Torr, or more typically less that $10^{-1}$ Torr. In some preferred embodiments, the low volatility ionization reagents of the present invention can have a vapor pressure at room temperature of or less that $10^{-2}$ Torr or, more preferably, less that $10^{-3}$ Torr.

In certain embodiments, the ionization reagent is a low volatility compound. The ionization reagent can be a crown ether, a glyme, a sugar, a cryptand, or a cavitand. These compounds can be used as ionization reagents and can form host-guest complexes with target analytes. These reagents include, but are not limited to, crown ethers (such as 12-crown-4, 15-crown-5, 16-crown-4, dibenzo 21-crown-7 or 18-crown-6), glymes (such as dimethoxyethane), sugars (such as sucrose, fructose, glucose), cryptands (such as 1,10-diaza-4,7,13,16,21,24-hexaoxabicyclo[8.8.8] hexacosane, kryptofix 222), and cavitands (such as cyclodextrin, calixarene, pillararene and cucurbituril). These compounds can be applied to the substrate material by a chemical process which can include immersion in a concentrated solution, liquid spray application, or vapor deposition. Certain target analytes will be detectable via ion-molecule chemistry which is attainable by introduction of low volatility reagents in a chemically doped swipe material for detection of the ionization reagent and target analyte complex.

"Crown ethers" are cyclic chemical compounds that consist of a ring containing several ether groups, e.g., oligomers of ethylene oxide or derivatives of catechol. "Glymes" are derivatives of glycol ethers, e.g., dimethoxyethanes, and include, monoglymes, diglymes, ethylglymes and tetraglymes. "Cryptands" are bi- and polycyclic multidentate compounds capable of encapsulating various cations. "Cavitands" are also container shaped molecules having cavities to engage in host-guest chemistry with guest molecules of a complementary shape and size.

The term "host-guest" complex as used herein generally refers to complexes that are composed of two or more molecules or ions that are held in a structural relationship, at least in part, by noncovalent bonding.

Accordingly, the ionization reagents of the present invention can form a host-guest complex with a target analyte. The host-guest complex can be held together in unique structural relationships by forces other than those of full covalent bonds. Host-guest chemistry encompasses molecular recognition and interactions through three-dimensional structures of the molecules to transiently bind one to another. The noncovalent interaction between the ionization reagent and the target analyte can be any type of, for example, hydrogen bonding, ionic bonding, van der Waals forces and hydrophobic interactions.

The host-guest complexes can be formed on the surface of, or embedded within the swipe material, or by interactions between the analyte and the reagent prior to desorption or ionization.

Swipes

The swipe, also referred to as a smear, wipe or substrate material, can be made of paper, metal, fabric, cloth, fibers, glass, or synthetic material. In one embodiment, the swipe is a fabric of polyester, muslin, or cotton. The swipe can also be in different shapes and sizes depending on the type of surface to be sampled. For example, the swipe can be a two-dimensional material. The two-dimensional material can be sheet-like in construction. The material can also be in a multitude of sizes and shapes. In another example, the swipe can be a swab or other three-dimensional swipe.

The swipe can be formed of material that can be resistant to chemical degradation during testing in the approximate pH range of 0.1 through 14 to avoid reacting or decomposing. The swipe can be white in color to aid test evaluation, can be heat resistant, absorbent and/or chemically resistant at elevated temperatures and can have hydrophilic properties for wetting when using fluid reagents. The swipe can also be roughened, for example, by use of a woven material, to aid in retrieving test sample particles from the environment. The swipe can also be thick enough to resist damage such as tearing during sampling, yet not be too thick such that heating of the test sample is inhibited. The swipe thickness can be optimized to achieve rapid, and even heating through the material layer.

The swipe, such as the swab, can be affixed to the end of a holder. The swipe can be permanently or temporarily affixed to the holder for ease of manipulation, usage and sampling. The swipe can also be for a single use, such as being disposable. In an exemplary embodiment, the surface of the swipe is clean, sterile, or uncontaminated with target analytes. The swipes can also be dry, damp or wet prior to use. When the swipes are used in a damp or wet state, the swipes can be dampened with a solution, such as distilled water, alcohol, or a working strength of a multipurpose detergent.

The swipes can also sample a dry, damp or wet surface. The swipes can be of absorbent material to collect the damp or wet samples. The sample surface can also be prepped by wetting or dampening with a solution prior to sampling with the swipe. The surface can be dampened with a solution, such as distilled water, alcohol, or a working strength of a multipurpose detergent.

One or more ionization reagents can be deposited on, embedded in or in association with the swipe to detect one or more target analytes. The ionization reagent association with the swipe can be through either physical entrainment, non-covalent bonds, or thermally labile covalent bonds. Each ionization reagent can allow the detection of a unique target analyte. The individual target analytes can be analyzed on the swipe at predetermined times and/or temperatures or temperature ranges. Each ionization reagent deposited on, embedded in or in association with the swipe can react to a specific target analyte.

The swipe can be substantially adapted to receive or present one or more ionization reagents to detect one or more target analytes. The swipe can have a plurality of test regions, quadrants or lines. A different ionization reagent can be deposited on each test region, quadrant or line of the swipe, generating a unique detection area of the swipe. The entire swipe can collectively generate a unique pattern or code for a particular target analyte or class of target analytes. The test regions, quadrants or lines can be detected separately or at the same time to generate the unique pattern or code for the particular target analytes or class of target analytes.

The ionization reagent can be either physically entrained in the swipe, bound to the swipe via non-covalent chemical bonds, or bound to the swipe via thermally labile covalent bonds.

Internal Standards

False-positives represent the number of times that a detector indicates that it has positively detected a target analyte when in fact none is present. If this rate is too high, the user loses confidence in the detector, or begins ignoring alarms that might be actual positive results. Some systems claim a low rate of false positives, but fail to disclose that there are many commonly encountered substances producing those false alarms, such as fuel, skin lotions, hair gels, perfumes, etc. False alarms can also be caused by detection of trace quantities of an analyte from another source.

False negatives represent the number of times that a detector fails to indicate that a target analyte is present when it actually is. False negatives are dangerous since that means people or devices are missing detection of target analytes. False negatives, at least for the known contraband substances, should be virtually zero.

Nuisance-alarms are alarms that result from the actual detection of a target analyte, but where the target analyte originates from another source rather than from the sample source. Interferences (or interferents) are chemicals that can interfere with the detection of target analytes. Interferences may produce either false-positives or false-negatives. False alarms can also be caused by chemical signature interferences between substances, such as cosmetics, toiletries, and the like, and a target analyte, making it difficult to differentiate a target analyte from an interferent.

False alarms and nuisance-alarms can be reduced by increasing detection specificity. Adjusting the ionization chemistry employed by using a different ionization reagent can significantly reduce false alarms and nuisance-alarms. By incorporating multiple ionization reagents to detect multiple target analytes, rates of false alarms and nuisance-alarms can be reduced. False alarms and nuisance-alarms can also be reduced by including positive and negative standards on the swipe. Internal standards ensure calibration. Calibrations can also take into account sampling conditions (temperature changes, humidity, altitude changes, etc.) in order to detect target analytes accurately.

Compound Detection

The swipe can be used to detect one or more target analytes. In one aspect, a surface can be swiped to transfer molecules off the surface to the swipe. The ionization reagent can further form an ionization reagent-target analyte complex to increase detection efficiency. In some embodiments, the molecules present on the swipe can be ionized to form charged complexes. The ionization process can be performed by a wide variety of techniques, depending on the phase (solid, liquid, gas) of the sample and the efficiency of the target analyte(s) in question. In one embodiment, the ionization process includes spatially uniform heating of the swipe to vaporize the molecules. Alternatively, heating can involve exposure of the swipe to spatially variant heating or employ a thermal ramp-up that can differentially vaporize the molecules depending on the temperature or in accordance with the spatially variant zones. In another embodiment, the swipe can include multiple ionization reagents. One ionization reagent can be a low volatility compound. Another can be a high volatility ionization reagent. Including both low and high volatility ionization reagents can vaporize the ionization reagents, and the target analytes in association with the ionization reagents, sequentially when exposed to a thermal gradient. The ionized molecules can then be analyzed, either as a single analysis or sequentially depending on vaporization/ionization of the molecules, and characterized in a mass spectrometer or other detector.

EXAMPLES

Materials and Methods

Ammonium nitrate residues were detected via API mass spectrometry. Ammonium ($NH_4^+$) was present at m/z 18, however, this was below the low mass cutoff of many mass spectrometers. In order to detect ionized $NH_4^+$ liberated by thermal desorption, a conventional thermal desorption swipe was chemically-modified to incorporate a crown ether reagent known to adduct $NH_4^+$. The ionization reagent yielded a higher molecular weight complex that was ionizable via atmospheric-pressure chemical ionization.

In these experiments, a solid reagent, either dibenzo-21-crown-7 (CAS#14098-41-0) or 18-crown-6 (CAS#17455-13-9), was entrained into the fabric of either muslin, cotton or polyester swipes. This swipe doping procedure consisted of drop-casting a known volume of a concentrated crown ether stock solution in acetonitrile onto the swipe material. The volatile solvent was allowed to dry at room temperature leaving the low vapor pressure crown ether in solid-state within the swipe matrix. The reagent-impregnated swipe was then used to swipe a known mass of solid ammonium nitrate residue from a TEFLON® surface. The contaminated swipe was placed on a thermal desorption stage which was pre-heated to 200° C. Ambient ionization mass spectrometry (specifically the DIRECT ANALYSIS IN REAL TIME® ionization source (JEOL/Ionsense) coupled with a 4000QTrap MS (ABSCIEX) operating in positive polarity was used to ionize the desorbed product and detect the ionized crown ether reagent+$NH_4^+$ complex. This experiment was performed in open atmosphere which contained levels of ambient ammonia and produced $NH_4^+$ upon positive ionization. Given the crown ether's high affinity for $NH_4^+$, ambient ammonia contributed to an elevated background in the mass channel for the reagent+$NH_4^+$.

In these experiments, isotopically-labeled $^{15}NH_4^{15}NO_3$ which shifts the reagent+$^{15}NH_4^+$ complex (M+19) to one higher mass unit than the product created by reagent+ambient $NH_4^+$ (M+18) was utilized. Nitrogen gas was used to purged or displace the air, however, the experiment was not performed in a hermetically sealed chamber.

Results

Figure 2:
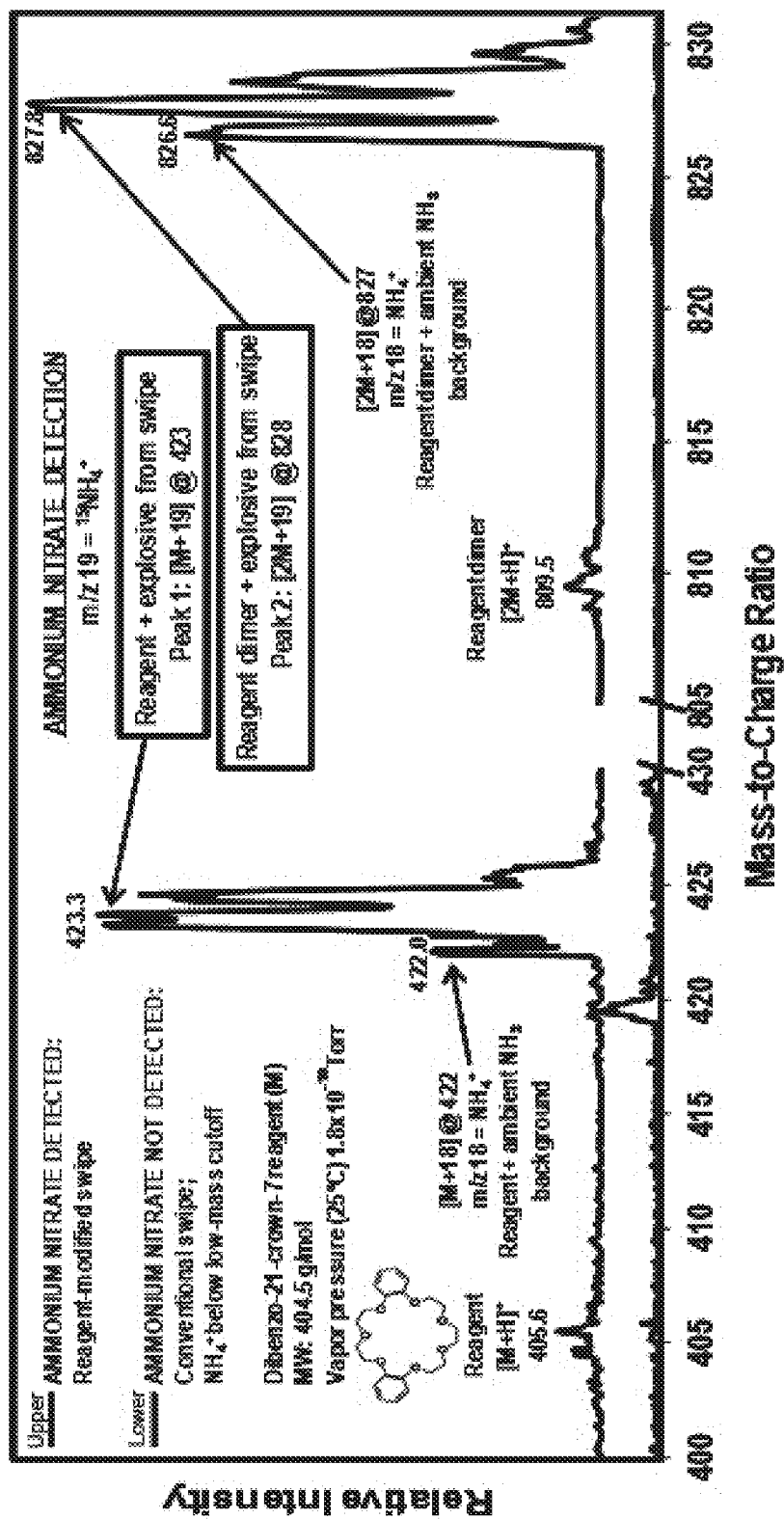
FIG. 2 is an overlay of two positive-mode mass spectra showing lack of detection of ammonium nitrate residue thermally-desorbed from a non-impregnated swipe (lower line) and detection of ammonium nitrate residue thermally-desorbed from the polyester swipe impregnated with dibenzo-21-crown-7 reagent M (upper line).

FIG. 2 is an overlay of two positive-mode mass spectra showing detection of ammonium nitrate residue thermally-desorbed from the polyester swipe impregnated with dibenzo-21-crown-7 reagent M. Without the impregnated swipe (lower line), a conventional swipe would not provide detection of ammonium above the low mass cutoff of many mass spectrometer systems. With the impregnated swipe (upper line), a swipe modified with an ionization reagent provides detection of ammonium indicating presence of the explosive. The single quadrupole mass spectrum scan shows detection of the reagent+$^{15}NH_4^+$ adducts at m/z 828 (2M+$^{15}NH_4^+$) and m/z 423 (M+$^{15}NH_4^+$). Free protonated reagent resides at m/z 405.6 (monomer) and 809.5 (dimer). Although the x axis (mass-to-charge) was magnified to visualize the higher mass region, the conventional swipe is devoid of ammonium-related peaks above the low mass threshold (~m/z 45) of this instrument. Peak intensities in the presence of ammonium residue versus a control swipe (reagent impregnated swipe without $^{15}NH_4^+$) at m/z 423 was S/N>3 and at m/z 828 was S/N>500. The same experiments with 18-crown-6 and $^{15}NH_4\,^{15}NO_3$ were performed and produced similar data with reagent+$^{15}NH_4^+$ adducts detected at m/z 547 (2M+$^{15}NH_4^+$) and m/z 283 (M+$^{15}NH_4^+$).

One skilled in the art will appreciate further features and advantages of the invention based on the above-described embodiments. Accordingly, the invention is not to be limited by what has been particularly shown and described, except as indicated by the appended claims. All patents, publications and references cited herein (including the following listed references) are expressly incorporated herein by reference in their entirety.

What is claimed is:

1. A thermal desorption swipe for detection of an analyte molecule comprising:
   thermal desorption substrate configured to collect a sample for analysis by mass spectrometry, the substrate formed of a fibrous material configured to collect a sample by swiping a surface and further constructed such that it can be thermally heated to desorb a target analyte into a vapor phase and capable of resisting decomposition at temperatures up to about 300° C.; and
   at least one thermally desorbable ionization reagent on the substrate, wherein the ionization reagent is physically entrained in the swipe prior to sample collection, and is capable of reacting with an analyte if present in the sample to form a reagent-analyte complex to increase detection efficiency such that the target analyte and ionization reagent can be co-vaporized into an ionization space of a spectrometric analyzing instrument to enhance detection of the analyte by mass spectrometry.

2. The swipe of claim 1 wherein the ionization reagent generates a charged complex with an analyte if present in the sample upon release of the reagent-analyte complex from the substrate.

3. The swipe of claim 1, wherein the ionization reagent is releasable into a carrier gas along with any target analyte molecules captured by the substrate during desorption in a detection instrument.

4. The swipe of claim 1, wherein the ionization reagent has a vapor pressure less than $10^{-2}$ Torr at room temperature.

5. The swipe of claim 4, wherein the ionization reagent has a vapor pressure less than $10^{-4}$ Torr at room temperature.

6. The swipe of claim 1, wherein the ionization reagent comprises at least one of β-keto esters, crown ethers, glymes, sugars, cryptands, amides, amines, chlorinated alkanes, organic bases, ionic dyes, and cavitands.

7. The swipe of claim 1, wherein the ionization reagent is further characterized as capable of forming a reagent-analyte complex with a target analyte associated with at least one of explosives, narcotics, chemical warfare agents, biological warfare agents, and toxins.

8. The swipe of claim 1, wherein the swipe further comprises a plurality of ionization reagents.

9. The swipe of claim 8, wherein the plurality of ionization reagents are associated with spatially separated portions of the swipe.

10. The swipe of claim 8, wherein the plurality of ionization reagents are uniformly applied to the substrate.

11. The swipe of claim 8, wherein the plurality of ionization reagents having different vaporization temperatures.

12. The swipe of claim 1, wherein the swipe further comprises at least one internal standard.

13. The swipe of claim 1, wherein the substrate comprises at least one of paper, fabric, cloth, fibrous matte, gauze, cellulose, cotton, flax, linen and synthetic fibers.

14. The swipe of claim 1, wherein the substrate has an extractables content of less than 3% during desorption.

15. The swipe of claim 1, wherein the ionization reagent is bound to the swipe via non-covalent chemical bonds, or bound to the swipe via thermally labile covalent bonds.

16. A method of detecting a target analyte comprising:
   swiping a surface with a swipe according to claim 1 comprising a substrate configured to collect a sample for analysis by mass spectrometry and at least one ionization reagent associated with the substrate adapted to form a reagent-analyte complex that enhances detection of the analyte by mass spectrometry;
   ionizing molecules present on the swipe following contact with the surface; and
   analyzing the ionized molecules by mass spectrometry to detect the target analyte.

17. The method of claim 16, wherein the step of ionizing molecules further comprises
   forming at least one charged complex of the reagent and a target analyte; and
   analyzing at least one charged species of the reagent-analyte complex to detect the target analyte.

18. The method of claim 16, wherein the step of analyzing the ionized molecules further comprises detection by ion mobility spectrometry, differential mobility spectrometry, field asymmetric spectrometry or mass spectrometry.

19. The method of claim 18, wherein the step of analyzing the ionized molecules further comprises detection by ion mobility spectrometry.

20. The method of claim 18, wherein the step of analyzing the ionized molecules further comprises detection by mass spectrometry.

21. The method of claim 16, wherein the method further comprises heating the swipe to vaporize the molecules present on the swipe.

22. The method of claim 16, wherein the swipe comprises multiple ionization reagents.

23. The method of claim 16, wherein the swipe comprises at least two ionization reagents having different vapor pressures and the step of ionizing further comprises exposing the swipe to a thermal gradient such that the ionization reagents are released sequentially.

* * * * *